Figure 1:
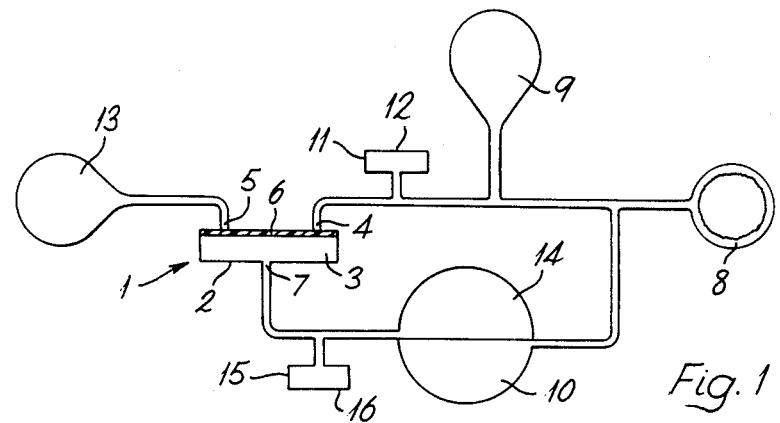

United States Patent [19]

Craggs

[11] Patent Number: 4,721,509
[45] Date of Patent: Jan. 26, 1988

[54] PROSTHETIC SPHINCTER DEVICES

[75] Inventor: Michael D. Craggs, London, England

[73] Assignee: National Research Development Corporation, London, England

[21] Appl. No.: 861,894

[22] Filed: May 12, 1986

[30] Foreign Application Priority Data

May 13, 1985 [GB] United Kingdom ............... 8512069

[51] Int. Cl.$^4$ ............................................. A61F 2/08
[52] U.S. Cl. ............................ 623/14; 128/DIG. 25; 128/1 R
[58] Field of Search ............... 623/14; 128/DIG. 25; 137/844, 851

[56] References Cited

U.S. PATENT DOCUMENTS

| | | | |
|---|---|---|---|
| 3,416,724 | 12/1968 | Lenkei | 137/851 |
| 3,744,063 | 7/1973 | McWhorter | 623/14 |
| 3,750,194 | 8/1973 | Summers | 623/14 |
| 3,759,289 | 9/1973 | DeWall | 137/844 |
| 4,408,597 | 10/1983 | Tenney | 128/DIG. 25 |
| 4,412,530 | 11/1983 | Burton | 128/1 R |
| 4,417,567 | 11/1983 | Trick | 128/DIG. 25 |
| 4,419,985 | 12/1983 | Trick | 623/14 |
| 4,549,531 | 10/1985 | Trick | 623/14 |
| 4,571,749 | 2/1986 | Fischell | 623/14 |
| 4,587,954 | 5/1986 | Haber | 128/DIG. 25 |

FOREIGN PATENT DOCUMENTS 2373272 8/1978 France ........................... 623/14

Primary Examiner—Richard J. Apley
Assistant Examiner—James Prizant
Attorney, Agent, or Firm—Cushman, Darby & Cushman

[57] ABSTRACT

A prosthetic sphincter device in the form of a closed pressure-fluid system operable by the recipient to control a body duct comprises a pressure-fluid reservoir (10), an inflatable duct-obviator (8) typically of cuff form, a pump (9) operable to deflate the cuff, and a control mechanism (1, 14, 15) operable normally to hold the cuff inflated at a preset pressure to close the duct, the mechanism being adjustable in situ post-operatively to vary the preset pressure. In a preferred form the control mechanism includes a valve (1) communicating the reservoir and cuff, and a preset pressure-fluid source (14) connected to hold the valve normally closed, this source including a self-sealing septum (16) allowing preset pressure adjustment by injection. The valve preferably has a through passageway defined at least in part by a flexible wall (6) externally subject to the preset pressure.

8 Claims, 6 Drawing Figures

U.S. Patent

Jan. 26, 1988

4,721,509

PROSTHETIC SPHINCTER DEVICES

This invention concerns prosthetic sphincter devices and more particularly such devices of the kind comprising a closed pressure-fluid system operable by the recipient to control a body duct.

Prior devices of this kind can be seen to involve in common four basic component parts, namely, a reservoir for the pressure fluid, an inflatable duct-obturating means, a pump facility operable by the recipient to inflate and/or deflate the obturating means, and a control mechanism for the pump facility, interconnected by tubing. Typically the device is wholly implantable, the pump facility is located subcutaneously for operation by palpation, and the obturating means is a cuff locatable around the urethra or other appropriate site to act against urinary incontinence when inflated and to allow micturition when deflated.

In an earlier form of these devices, the pump facility and control mechanism comprise separate pumps connected, by way of valves, between the reservoir and cuff respectively for inflation and deflation. The valves are essentially of unidirectional flow type to direct the pumped fluid appropriately, and also serve a pressure relief function to ensure that the cuff is not inflated above a preset pressure level.

In a subsequently developed form of the devices in question there is a single pump connected, by way of the control mechanism, between the reservoir and cuff to deflate the latter. In this case the reservoir serves to hold fluid at a preset pressure and the control mechanism allows a restricted flow to the cuff to maintain the same normally inflated at such pressure.

It will be appreciated, from obvious considerations and the explicit indication for the last-mentioned form of device, that devices of the kind in question have a normal operational state entailing inflation of the obturating means. It is to be noted at the same time that the pressure of such inflation should not be significantly higher than the minimum level necessary to attain the desired result otherwise necrosis can occur in the adjacent tissue subjected to that pressure. Now, while it may appear that the above forms of prior device can be satisfactory in this respect because each has a control mechanism operable to effect a normal preset inflation pressure, this assumes that an initial setting is satisfactory in all circumstances and can be chosen appropriately. In fact, experience shows that the pressurised tissue can, with time, harden post-operatively so that a requirement can arise for an increased inflation pressure. An obvious disadvantage of the prior devices in this connection is that such a requirement is only accommodated by change of a component part and this necessitates further surgery.

An object of the present invention is to avoid this disadvantage and, to this end, the invention provides a device of the kind in question in which the control mechanism is effective normally to preset a maximum inflation pressure level, such mechanism being adapted to allow adjustment of such preset level in situ post-operatively.

Preferably the control mechanism of the invention involves a valve for communicating the reservoir and obturating means, and a source of fluid at preset pressure connected with said valve to hold the same normally closed, said source including a self-sealing septum allowing flow of fluid therethrough by way of an injection instrument to adjust said preset pressure.

In a more particularly preferred form of the invention there are separate inflation and deflation pumps, there is a first reservoir to hold working fluid and a second reservoir to hold fluid at said preset pressure, and said valve has a through passageway defined at least in part by an element movable to open and close the same, the deflation pump, first reservoir and obturating means being connected with said valve at one end of said passageway, the inflation pump being connected with said valve at the other end of said passageway, and the second reservoir being connected with said valve to effect passageway-closing movement of said element.

The valve for this last purpose is suitably of a flap or equivalent form with the movable element being a flexible wall.

Lastly in this more general discussion of the invention, it is to be noted that the proposed self-sealing septum affords advantages additional to that of allowing upward adjustment of the preset pressure and, for this reason, another such septum is preferably connected with the first reservoir.

Figure 5:
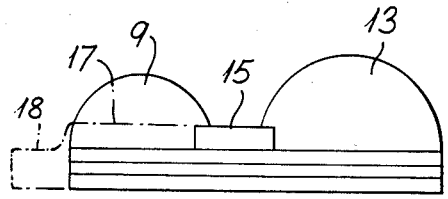
Figure 6:
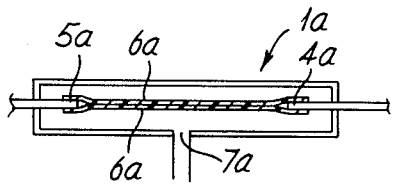

In order to facilitate a fuller understanding of the invention the same will now be described by way of example with reference to the accompanying drawings, in which:

FIG. 1 schematically illustrates the initially developed form of the invention,

FIGS. 2 to 5 illustrate detail of both an initially and subsequently developed construction for the pump facility and control mechanism valve of FIG. 1, and FIG. 6 illustrates detail of a modification arising from the most recent development of the invention.

The device of FIG. 1 comprises a valve 1 of the flap form mentioned above. This valve is constituted by a body 2 defining a chamber 3 having three ports. Two of these ports denoted at 4 and 5 open into a wall portion of the chamber covered by a flexible flap 6 sealed around its edges with the chamber. The remaining port 7 opens into the chamber at another wall portion not covered by the flap.

An inflatable obturating means in the form of a cuff 8, a bulb-form deflation pump 9, a first reservoir 10, and a first liquid access chamber 11 partly defined by a self-sealing septum 12 are connected in mutually communicating manner with the port 4 of valve 1.

An inflation pump 13 of similar bulb form to pump 9 is connected with the port 5 of valve 1.

Lastly in the device, a second reservoir 14 and a second liquid access chamber 15 with self-sealing septum 16, respectively similar to reservoir 10 and chamber 11, are connected in mutually communicating manner with the port 7 of valve 1.

Use of the device involves complete implantation, with the cuff located around the urethra or other appropriate urinary duct site to be controlled, the pumps and fluid access chambers located subcutaneously respectively to facilitate palpation and injection instrument access, and the reservoirs are located abdominally or elsewhere in a site subject to forces associated with stress incontinence. Obviously also, the system is filled with a pressure fluid, conveniently by way of the septa 12 and 16, the fluid in the second reservoir 14 being pressurised to a preset level which is initially judged to be a minimum appropriate to effect urinary continence with the cuff inflated.

In operation, cuff inflation is effected by operation of the pump 13 to propel fluid at high pressure through the valve 1 into the cuff and the other components communicated therewith. This pressure will be above the preset pressure level within the second reservoir and acting also within the main body of the valve chamber, so that the valve flap lifts from the ports 5 and 4. Any excess of cuff pressure relative to the preset level will similarly, after inflation, maintain the valve open to allow a return flow of fluid to the pump until the cuff pressure decreases to the preset level, whereafter the valve closes.

In the event that muscular forces occur which elevate the bladder pressure above the preset level in the cuff, these same forces will at the same time normally act on the first reservoir to correspondingly elevate the cuff pressure, and also on the second reservoir to hold the valve closed. Stress incontinence, which can result from coughing, sneezing and other actions causing high transient increases in intra-abdominal pressure is accordingly accommodated without permanent application of an excess cuff pressure.

Cuff deflation to allow micturition is, of course, effected by operation of pump 9. Such operation will, like that for inflation, generate a pressure in excess of the preset level and so open the valve for fluid flow. This flow conveys fluid to the pump 13 where it is, upon ceased deflation pumping, held by valve closure. Also, upon valve closure, the correspondingly reduced fluid volume in the cuff and associated components redistributes by re-entering the pump 9 and so the cuff pressure is reduced to a non-occluding level. This overall action is enhanced by locating the pump 9 closer to the valve than the cuff in terms of tubing connection lengths so that the greater drag in the path to the cuffs causes a preferential return fluid flow to pump 13.

As noted above, any incidence of post-operative incontinence due to inadequacy of the preset cuff inflation pressure in the short or longer term can be accommodated by injection of fluid through the septum 12 to adjust this last pressure upwardly.

The septa 12 and 16 can serve an additional function in the event that the device suffers a post-operative fluid leakage. It is usual in the prior devices for use to be made of a fluid which is radio-opaque in order to facilitate detection of the site of such leakage. However, leaked fluid can in practice dissipate before examination is conducted to localise the leak. In the present case such examination is facilitated by the ability to re-fill the device. The septa can, of course, also be used for fluid removal if appropriate.

Construction of the device of FIG. 1 suitably involves a medical grade silicone rubber almost in its entirety, with mesh reinforcement in some areas such as the pump bulbs, such material being long proven in terms of biocompatibility and other appropriate properties.

In matters of detailed construction, the cuff may be of any suitable geometry but normally will be of closed loop form or its equivalent, like a jubilee clip for example for purposes of adjustability. The two reservoirs are preferably each of hemispherical form mounted in mutual back-to-back assembly, as indicated by FIG. 1, with their common wall being rigid. The control valve, pumps and liquid access chambers are preferably formed by a common assembly such as shown by FIGS. 2 to 5.

Figure 2:
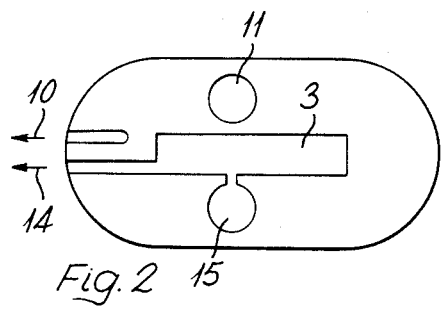
Figure 3:
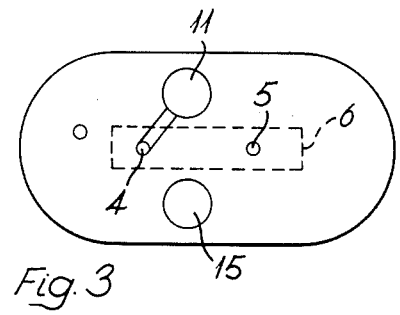
Figure 4:
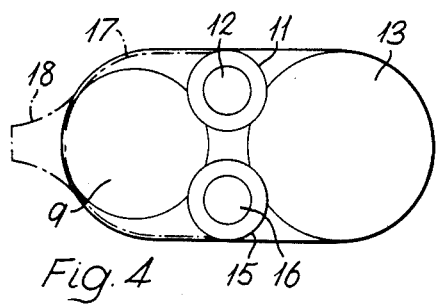

In an initial embodiment this assembly was of sandwich form made up from three sub-components respectively illustrated by FIGS. 2 to 4 in plan view for the base, middle and top, and with the overall assembly shown by FIG. 5 in side elevation.

The base of FIG. 2 is essentially a slab which is recessed on its upper side to provide the valve chamber 3, part of each of the fluid access chambers 11 and 15, and respective passageways for communication with the reservoirs 10 and 14.

The middle of FIG. 3 is also essentially a slab of like perimeter to that of the base for registration thereover. This middle slab is apertured to provide the ports 4 and 5, a flexible sheet defining the flap 6 being sealed around its edges below the slab to cover the ports. Aperturing is also effected to continue the chambers 11 and 15, and to communicate chamber 11 with the passageway to reservoir 14. In addition the upper surface is recessed to communicate the chamber 11 with the port 4.

The top of FIG. 4 has a like plan perimeter to that of the middle for registration thereover, but has upward convex formations as seen from FIG. 5. Two of these formations are hemispherical to define the bulbs for the pumps 9 and 14 and, in assembly, they respectively overlie the port 4 and reservoir 14 aperture on the one hand, and the port 5 on the other hand. The remaining formations define the septa 12 and 16 with respective side walls thereuaround.

All of the elements of this assembly are suitably of silicone rubber except that the base is preferably stiffened with a sheet of ceramic or other material of appropriate properties.

It is thought useful to provide a template (not shown) to aid localisation of the septa of this assembly for the purposes of fluid transfer to or from the assembly following implantation. This template will generally match, at least in plan outline, the upper surface of the assembly and have a respective injection instrument guide bore in a position corresponding to the centre of each septum. In use, the assembly is manually located and the template positioned on the skin thereover in the best possible register. Even allowing that this register may not be perfect, the template bores nevertheless can then serve to guide an injection instrument appropriately to each septum.

Further development has given rise to an improved embodiment derived from that detailed in FIGS. 2 to 5. In this development the sandwich construction is simplified to require only two subcomponents. The chambers 11 and 15 have rigid side walls to avoid any risk of puncture during injection of the septa. The assembly has an elevated side wall around the deflation pump 9, as indicated in chain line at 17 in FIGS. 4 and 5, to obviate the risk of undesired deflation operation. The base portion of the assembly is formed with a flared projection in the end region where tube connections are made to the reservoirs 10 and 14, as indicated in chain line at 18 in FIGS. 4 and 5, to act against failure of such connections.

The most recent development of the invention contemplates yet further improvement.

Firstly, benefit is thought to stem from use of a modified valve comprising opposed flexible walls interconnected in the manner of a flat tube of which the interior defines the valve passageway and the exterior is subject to the relevant preset pressure within a surrounding chamber. This is schematically illustrated in FIG. 6 which deploys the the reference numerals of FIG. 1 for corresponding elements but with the addition of "a" to distinguish the former. Operation of the valve of FIG. 1 could be subject to variation by distortion of the wall 6 together with the adjacent chamber wall and the provision of the rigid base in the assembly of FIGS. 2 to 5 is intended to obviate such variation. Operation of the valve of FIG. 6 is not subject to such variation in normal circumstances and a rigid base is accordingly unnecessary. This is beneficial in terms of simplified construction and, more particularly, in reducing the need for the use of differing materials within the overall device. Also, operation of the valve of FIG. 1 can vary due to creep of the flexible wall which must flex resiliently. In the valve of FIG. 6 operation can involve resilient movement at the ends of the passageway whereby the walls 6a flex without significant creep-inducing stress.

Secondly, benefit thought to be possible with use of separated reservoirs which are each wholly spherical, this arrangment being compatible with an optimum pressure/volume operating characteristic for the reservoirs. Also, separation of the reservoirs avoids the need for a rigid common wall and so further reduces the need for use of different materials.

I claim:

1. A prosthetic sphincter device in the form of a closed pressure-fluid system operable by the recipient to control a body duct, which device comprises:
   first and second reservoirs respectively to hold working pressure fluid at a varying pressure and controlling pressure fluid at a preset pressure;
   inflatable duct-obturating means;
   first and second pumps respectively operable to inflate and deflate said obturating means;
   a valve having a through passageway defined at least in part by an element movable to open and close the same; and
   a chamber having a wall in the form of a self-sealing septum allowing flow of fluid therethrough by way of an injection instrument;
   said first reservoir, second pump and obturating means being connected with said valve at one end of said passageway to form a first end portion of a working fluid circuit;
   said first pump being connected with said valve at the other end of said passageway to form a second end portion of said working fluid circuit;
   said second reservoir being connected with said valve to form a controlling fluid circuit operable to effect passageway closing movement of said element under said preset pressure;
   said first and second pumps being operable to convey fluid in said working circuit respectively from said first to second end portion thereof and in the opposite manner, while in each case said controlling circuit acts on said valve to hold said end portions of said working circuit to and from which fluid is conveyed respectively at an elevated pressure not greater than said preset pressure and at a relatively lower pressure, to cause deflation and inflation of said obturating means; and
   said chamber being connected with said second reservoir in said controlling circuit to allow adjustment of said preset pressure.

2. A device according to claim 1 wherein said valve is of a flap form with said movable element being a flexible wall.

3. A device according to claim 2 wherein said movable element comprises two flexible walls interconnected in the form of a lay flat tube of which the interior defines said passaeway and the exterior is subject to said preset pressure.

4. A device according to claim 1 comprising a further chamber having a wall in the form of a self-sealing septum, such further chamber being connected with said first reservoir.

5. A device according to claim 1 wherein said second pump is connected to said valve by way of a pressure fluid flow path of lesser resistance than that from such pump to said obturating means.

6. A device according to claims 1 wherein said pumps together with each said chamber are collectively located in an assembly on one side of a common base structure including said valve, and said reservoirs are each of substantially spherical shaping and remotely connected with said assembly.

7. A device according to claim 6 wherein each said chamber includes a rigid side wall structure extending from its septum towards said base member.

8. A device according to claim 1 wherein said obturating means is in the form of a cuff.

* * * * *